(12) United States Patent
Anhalt

(10) Patent No.: US 9,187,613 B2
(45) Date of Patent: Nov. 17, 2015

(54) USE OF FINELY DISPERSED METAL PARTICLES IN A MATERIAL, A SKIN PATCH AND AN ORTHOPEDIC ARTICLE

(75) Inventor: Klaus-Peter Anhalt, Rhumspringe (DE)

(73) Assignee: OTTO BOCK HEALTHCARE GMBH, Duderstadt (DE)

(*) Notice: Subject to any disclaimer, the term of this patent is extended or adjusted under 35 U.S.C. 154(b) by 587 days.

(21) Appl. No.: 13/194,264

(22) Filed: Jul. 29, 2011

(65) Prior Publication Data

US 2011/0280957 A1    Nov. 17, 2011

Related U.S. Application Data

(63) Continuation of application No. PCT/EP2010/000540, filed on Jan. 29, 2010.

(30) Foreign Application Priority Data

Jan. 30, 2009 (DE) .......... 10 2009 006 941

(51) Int. Cl.
| | |
|---|---|
| A61K 33/38 | (2006.01) |
| A61K 9/70 | (2006.01) |
| C22C 5/06 | (2006.01) |
| C08K 3/08 | (2006.01) |
| C08K 3/00 | (2006.01) |

(52) U.S. Cl.
CPC . *C08K 3/08* (2013.01); *C08K 3/005* (2013.01); *C08K 2003/0806* (2013.01); *C08K 2201/014* (2013.01); *Y10T 428/249921* (2015.04)

(58) Field of Classification Search
None
See application file for complete search history.

(56) References Cited

U.S. PATENT DOCUMENTS

| | | | |
|---|---|---|---|
| 5,215,520 A * | 6/1993 | Shroot et al. ............ 604/20 |
| 5,322,520 A | 6/1994 | Milder | |
| 7,390,774 B2 | 6/2008 | Ghosh et al. | |
| 8,256,149 B2 * | 9/2012 | Nathamuni Balaji et al. .... 38/97 |
| 2007/0077312 A1 | 4/2007 | Bechert et al. | |
| 2009/0149947 A1 * | 6/2009 | Frohwitter ............ 623/1.42 |
| 2010/0151032 A1 | 6/2010 | Bechert et al. | |

FOREIGN PATENT DOCUMENTS

| | | | |
|---|---|---|---|
| CN | 1687200 A | | 10/2005 |
| CN | 1817138 A | | 8/2006 |
| CN | 101926784 | * | 12/2010 |
| DE | 1176855 B | | 8/1964 |
| DE | 2950994 A1 | | 6/1981 |
| DE | 3228849 A1 | | 2/1984 |
| DE | 3830359 A1 | | 12/1989 |
| DE | 69216528 T2 | | 5/1997 |
| EA | 006183 B1 | | 10/2005 |
| EP | 38793 | * | 10/1981 |
| EP | 0535955 B1 | | 1/1997 |
| JP | 1250411 A | | 10/1989 |
| JP | 2009138072 | * | 6/2009 |
| KR | 20080066316 A | | 7/2008 |
| RU | 2292224 C1 | | 1/2007 |
| RU | 2314834 C1 | | 1/2008 |
| WO | WO-2004089431 | * | 10/2004 |
| WO | 2005023206 A2 | | 3/2005 |
| WO | 2008027753 A1 | | 3/2008 |

OTHER PUBLICATIONS

International Search Report for International Patent Application No. PCT/EP2010/000540, mailed May 26, 2010.
Database WPI Week 198946, XP-002582039, Thomson Scientific, London, GB, 1989.
Database WPI Week 200921, XP-002582263, Thomson Scientific, London, GB, 2009.
Ionpure Brochure, Ishizuka Glass Co., Ltd., Nagoya, Japan, 6 pp. (available at least as early as Jan. 30, 2009).

* cited by examiner

*Primary Examiner* — Alton Pryor
(74) *Attorney, Agent, or Firm* — Holland & Hart

(57) ABSTRACT

A material which is provided for use in direct contact with the skin of a user and which contains a percentage in silver that is finely dispersed in said material. The material is provided with a content in another metal that is finely dispersed in the material in addition to the silver content. The metals of the group including aluminum, magnesium, zinc, bronze, titanium and platinum are suitable either individually or in combination and in amounts between 0.1 and 1% by weight. The use of the metal particles is also suitable to conceal discolorations in a pigmented or dyed synthetic material when the material is used in air or on the skin. The metal particles do not impair the properties of the material. The material can be used to produce skin patches of any kind, especially for use in orthopedics.

19 Claims, No Drawings

USE OF FINELY DISPERSED METAL PARTICLES IN A MATERIAL, A SKIN PATCH AND AN ORTHOPEDIC ARTICLE

The invention concerns concealing of material discoloration in use in air or on the skin, caused for example by contact with perspiration, particularly in a material that itself is not a metal, should not substantially conduct electricity, and is intended for use in direct contact with the skin of a user. The invention also includes use in various skin patches and cushions and in orthopedic articles.

It is known that plastic products become discolored during use on the skin due to UV radiation, but also other environmental effects, such as contact with bodily fluids and perspiration. A particularly frequent occurrence is yellowing of white or lightly dyed plastics.

Yellowing and discoloration occurs for example in the case of orthopedic cushions, primarily when these cushions are light or skin-colored. As such discoloration can give the plastic component a soiled and aesthetically unpleasant appearance, they must be prevented or concealed.

An attempt is often made to counteract discoloration by using a higher pigment content. As a rule, however, this impairs the mechanical properties of the plastic components, which may be highly important in medical or orthopedic cushions. One therefore cannot increase the percentage of pigments or dyes used as additives so drastically that discoloration could thus be completely prevented.

In standard dyeing, the dyed plastic component becomes darker over time as a result of absorption of light due to two effects, the desired effect of the pigment and the undesired discoloration. Moreover, it is only possible to conceal the actual discoloration by using a suitable dye having an absorption spectrum in which the color of discoloration is also absorbed.

There is therefore a need for alternatively dyed plastic components for medical and orthopedic technology. Numerous plastic components that come into direct contact with the body are required for both medical and special orthopedic purposes. These include various cushions, orthotic components, prosthetic components, and other orthopedic equipment.

The method is also known of including silver in materials in order to give them an antibacterial effect, particularly if the materials are intended for use in lengthy and intensive contact with the skin. Silver is particularly preferred for use with materials that come into contact with perspiration in order to prevent odor formation due to bacterial decomposition products in perspiration, or also in the medical area for wound dressings and for treating particular skin diseases such as neurodermatitis.

In an example of a known method, textiles are provided with silver fibers or with a silver-containing coating for this purpose. Surface coatings may also be provided for refrigerators, kitchen furniture, and technical components that are frequently touched by different people, such as light switches or doorknobs—particularly in hospitals. These coatings may constitute thin oil or polymer films. Antibacterial enamels and ceramics are known, as well as silver-containing plastics for use in medical and orthopedic technology.

The antibacterial effect of the silver is attributed to the silver ions that are readily generated on contact with the skin, in particular due to skin fluids and perspiration. In the course of use, the silver undergoes partial oxidation. In use on the skin, black silver sulfide is produced, which frequently makes the product containing silver unsightly. For textiles and polymers containing silver, therefore, the colors grey, anthracite grey, and black are preferred, as they make the formation of silver oxide or silver sulfide unnoticeable. However, problems occur with the use of light or skin-colored rubber or plastic cushions, e.g., in the area of orthopedics for prostheses and other orthopedic aids.

So-called liners, manufactured from soft elastic polymers (plastics, homo- or copolymers, polymer mixtures, rubbers), are used for example as connecting elements and cushions between limb prosthesis stumps and the accompanying prosthesis shafts. Among other types, silicone liners and polyurethane liners are on the market. In this case, the silicone and polyurethane materials are composed exclusively of silicone and polyurethane polymer gels and as such are transparent, and it is only when pigments are used that they become opaque or colored. Because of the strong effect of perspiration and general body fluids, plastic components used in orthopedic medicine quickly become unsightly, and this applies in particular to highly moisture-permeable plastics and gel polymers. The only approach that has helped to date against the inevitable discoloration caused by pigmented or dyed plastics is extensive pigmentation and dyeing in a suitable optical absorption range. From the standpoint of materials technology, however, the addition of large amounts of dye and pigment is frequently undesirable, as this may sharply impair physical and mechanical properties that are indispensable for the desired effect of the product. If silver is added to such liners, generally by mixing it into the plastic mixture in finely dispersed form, the liners quickly become unsightly despite pigmentation because of their extensive exposure to perspiration. The only approach that helps against this is dyeing using a grey or dark-grey to black color, which is often undesirable.

The purpose of the invention is to prevent or better conceal discoloration of colored or dyed plastic components and to provide materials, particularly those that are intended for use in direct contact with the user's skin and contain a percentage of silver finely dispersed in the material as an antibacterial agent, with properties such that the product remains virtually unchanged and attractive from a visual standpoint over a long period without impairing its material properties.

This purpose is achieved by using finely dispersed metal particles according to Claim 1, a material according to Claim 8, a skin patch according to Claim 13, and an orthopedic article according to Claim 14.

Generally, the invention describes the use of finely dispersed metal particles, particularly from the group aluminum, magnesium, zinc, bronze, titanium, and/or platinum, in a material, preferably a plastic material, which may contain silver as an antibacterial agent, in order to conceal discoloration and/or silver discoloration when the material is used in the air or on the skin.

The material should preferably be used in a skin patch or an orthopedic cushion.

Here, "orthopedic cushion" refers to any cushion used in orthopedics technology, including cushions used for medical purposes. Such cushions are primarily cushioning pads of various forms, which e.g. may be glued onto the skin in order to achieve a cushioning effect at certain points on the body, or prosthesis coverings, orthotic coverings, prosthesis shafts, prosthesis liners, shoe sole inserts, orthopedic shafts and shoes in general, or orthopedic synthetic stockings.

The cushion may also be provided, at least on one side, with a textile cover, or it may be coated on one or both sides.

In a particularly preferred application, the material according to the invention is used in an amputation stump liner or limb (amputation) stump liner and/or an orthopedic cushion in the form of an amputation stump liner. An amputation stump liner constitutes the cushioned transition between a limb stump and a prosthesis holder, specifically a prosthesis shaft, and is essentially composed of a polymeric elastic material that in this case is mixed with the added metal particles, and if desired, also with silver. Connections for prostheses, anchorings, valves and the like can further be provided on the liner. This is known to a person skilled in the art and need not be described here in further detail. Moreover, the liner may be equipped on one or both sides with a textile covering (i.e., either only on the side in contact with the skin, only on the side away from the skin, or on both sides). This covering should preferably be a thin deposited layer such as a CVD layer. The material of the stump liner should preferably be a homopolymer or copolymer material or a mixture of several plastics. The plastic of the liner should preferably be elastic, and even more preferably, should be in the form of a gel, and should be equipped with special mechanical properties depending on the purpose of application.

In addition to stump liners, the following orthopedic cushions are particularly well-suited to be equipped according to the invention: general orthopedic cushioning pads, prosthesis coverings, orthotic cushions, prosthesis shafts, components of supporting devices, shoe sole inserts, or orthopedic synthetic stockings used as knitted fabrics in the same manner as liners in order to cushion orthopedic holding devices or prosthetics.

Generally speaking, the invention also includes the use of the orthopedic cushions according to the invention in more complex orthopedic articles or orthopedic articles such as those equipped with the cushion according to the invention.

The metals used as a supplement to silver or without silver may be metals in nanoscale or colloidal form, powder particles, fine granules, or flakes or scales, chips or filaments. Commonly sold metal powders are also suitable for the invention. Corresponding powders are also used, for example, in the jewelry or paint industry. The particle size is generally between 1 and 100 µm, with a minimum particle thickness for flake-type and nanoscale particles being 0.1 µm.

The metal particles used according to the invention have no black oxides or sulfides, and the metallic dye effect produced by them shows virtually no change during use of the products manufactured from the material. Surprisingly, it has been found that compared to pigments used as general anti-yellowing agents, substantially lower amounts, and specifically only 5 to 10% of the minimum pigment or dye content required for an operating effect, are needed to achieve a sufficient effect of concealing discoloration on contact with the skin of a user or perspiration. Particles composed of aluminum or an aluminum alloy should preferably be used. Greater glossiness is imparted to the coloring of the plastic because of the presence of metal particles and dye or pigment particles. Highly appealing optical effects also result from the use of translucent dyes in combination with the metal particles according to the invention.

The metal content, i.e. the percentage of metal particles with respect to total weight, should preferably, to supplement existing silver content, be at least 0.01% by weight, and more preferably at least 0.1% by weight, with a content of 0.5% by weight being even more preferable. A value of up to 1% by weight, or a maximum of 3% by weight, is considered sufficient to achieve the desired effects. The silver content used in materials containing silver for antibacterial purposes (plastics and textiles) should preferably range from less than 0.01% by weight to a maximum of 0.1% by weight.

Therefore, a considerable advantage of the invention already lies in the fact that when it is used in plastics, a smaller amount of additive is used for dyeing when pigments/dyes and metal are used than if only pigments or dyes were used. If applicable, one may even dispense completely with the use of pigments and dyes.

An additional and even more significant advantage can be seen in the fact that adding metals in such a small amount has virtually no effect on the mechanical properties of a plastic, which is particularly important for gel-based and soft plastics. This is particularly significant in the case of functional products, in which the properties of the materials are of decisive importance. Plastic cushions used in medicine and orthopedic technology, orthotic components, and components of supporting devices and similar products in particular must possess highly specific elastic properties, strength, stretching properties, etc.—if applicable, even anisotropic properties—and these properties must not be impaired by additives.

An additional advantage of the invention is to be seen in the fact that the plastic material possesses a silver or bronze coloration, and thus a highly attractive appearance. This is particularly pronounced in the presence of colored pigments other than white and black and in the case of translucent pigments.

It was also observed that metallization, if applicable in addition to silver, may have a positive effect on the user with respect to neuralgia and phantom pain. This may be attributable to the capacitive action of the metal used.

Insofar as the invention is used in products that also contain silver, it is surprising that apparently no local elements are formed, even in the case of moisture-permeable and swellable plastics and textiles. One would assume per se that the elements below silver in the electrochemical series, such as aluminum, would reduce the formation of silver ions, which are considered to have an antibacterial effect, and thus eliminate this effect. Conversely, the elements above silver in the electrochemical series could oxidize and consume the sugar too rapidly. Neither of these phenomena occur, as we were able to experimentally demonstrate. The silver concentration and silver action remain unaffected, even when swelling tests are conducted with the silver-doped materials. For example, we were unable to detect any silver losses or measure any conductivity in silver-doped silicone liners that had been immersed in saline solution for a week. There is therefore no need to fear that the material according to the invention will lose its effect on contact with skin moisture or perspiration. Accordingly, there are no corresponding disadvantages due to foreign metals corresponding to the aforementioned advantages.

Examples of suitable basic materials, which if applicable are mixed with silver and the additional metal intended primarily to act as a metal dye, include polymers (natural or synthetic, i.e., plastics of all kinds, rubber, latex, gutta-percha) and textiles (natural fibers and fleeces, synthetic fibers and fleeces), but also other materials, which themselves are not metals and preferably should not conduct or only slightly conduct electricity, e.g., ceramics.

Plastics particularly well-suited for use are polymeric or copolymeric elastic plastics, soft plastics, or polymer gels.

Particularly preferred is a material according to the invention that is intended for use in direct contact with the skin of the user and contains a percentage of silver finely dispersed in the material as an antibacterial agent, with said material also containing, in addition to the silver, a percentage of metals finely dispersed in the material from the group aluminum, magnesium, zinc, bronze, titanium, or platinum, individually or in combination, with aluminum or an aluminum alloy being especially preferable.

Generally, the invention also includes a skin patch composed of the material according to the invention. This may be any skin patch that has also been provided with silver in prior art, specifically cushioning pads, prosthesis linings, orthotic components, components of supporting devices, textile patches such as elastic bandages, amputation stump liners, prosthesis shafts, prosthesis holders, and skin patches for thermal insulation. In a particularly preferred embodiment, one uses the material according to the invention for an amputation stump liner or a skin patch in the form of an amputation stump liner.

The invention further comprises an orthopedic article having the material as a cushion or insulating material, specifically for orthopedic purposes, and also comprises use of the material for holders or supporting devices on the human body, orthotics and orthotic components, shaft cast resins, textile coatings, and textile impregnation.

Additional products that can be advantageously manufactured from or with the material according to the invention are shoe sole inserts, sitting cushions for chairs, wheelchairs and beds, arm supports, and support hose and stockings.

In the following, the invention will be described in greater detail by means of examples, which are intended for illustrative purposes but do not limit the scope of the invention in general.

The polymer recipes described below were used as a material base. To the material base or base material, silver in the desired form and/or at least one additional metal from the group of aluminum, magnesium, zinc, titanium, platinum, or bronze was added. The silver was added to all materials/samples in the form of a commercially available additive having a silver content of 1.6% by weight, with said additive being added in an amount of 0.6% by weight with respect to the base materials.

I. The following are examples of suitable base materials that were used:

1.) Silicones:
RTV-Silicone gels (dual-component gels polyaddition), e.g., Rhodia® 4411 or 4420, mixed if applicable with 1 to 15% by weight of silicone fluid or silicone oil.

Specific examples of suitable recipes for silicone materials are:
Rhodia® 4411 100: 12
Rhodia® 4420 100: 10
Rhodia® 4420 100: 10 with 5% silicone fluid 0.65 cst
Dow Corning Silastic® T2 100: 10, with or without 10% Dow Silicone Oil 200 (350 cst)
Wacker Elastosil® RTV 4644 100: 10, with or without 15% Silicone Oil Wacker AK 1000
each of which is miscible with the optimum amount of 0.05 to 0.15% by weight Al powder 2.) Polyurethanes:
Polyurethane from polyether polyol with aliphatic isocyanate 100: 13, 0.1 to 0.5% Coscat® catalyst, viscosity reducer BYK A 535;
or Conathan TU 401 with TU 810 100: 51
each of which is miscible with the optimum amount of 0.05 to 0.15% by weight Al powder 3.) Block Copolymers:
SEBS:
15-30% Kraton 1651G, 60 to 75% med. white oil, 0-1% antioxidant, 0-25% viscosity reducer (e.g., petroleum ether)
SEEPS:
10-20% Septon 4044, 70-80% med. white oil, 0-1% antioxidant, 0-20% viscosity reducer (e.g., petroleum ether) each of which is miscible with the optimum amount of 0.01 to 0.2% by weight Al powder II. The following recipes were subjected to comparative measurements in order to influence mechanical properties by means of pigments and metal particles. The results are shown in Table 1.
(Basic Material with Silver Added, as Specified Above)
Recipe A: Rhodia 4411 100: 12 (reference, no metal, no pigment)
Recipe B: Rhodia 4411 100: 12 with 1% by weight Elastosil Colored Pigment FL
Recipe C: Rhodia 4411 100: 12 with 3% by weight Elastosil Colored Pigment FL
Recipe D: Rhodia 4411 100: 12 with 0.1% by weight Al powder

|  | Recipe A (Reference) | Recipe B (1% pigment) | Recipe C (3% pigment) | Recipe D (0.1% Al powder) |
|---|---|---|---|---|
| Tensile strength (N/mm$^2$) | 1.36 | 1.45 | 1.20 | 1.41 |
| Elongation at break (%) | 522 | 539 | 480 | 585 |
| 400% tension (N/mm$^2$) | 0.8572 | 0.8578 | 0.9017 | 0.7184 |
| Tear strength (N/mm) | 7.12 | 7.46 | 6.90 | 7.86 |
| Coefficient | 1.59 | 1.69 | 1.33 | 1.96 |

Discussion of Comparative Measurement Results:

Recipe B contained 1% by weight of colored pigment, which is to be considered the minimum required to conceal (slight) greying due to silver. In cases of more severe discoloration, such as may occur due to contact with sulfur compounds, the silver-based liner requires a sharply higher dye concentration of at least 3% (see Recipe C). In both cases, Recipes B and C, the same grey coloring pigment was used. The visually observed degree of coverage for Recipe Example D was 0.1% by weight aluminum powder, roughly corresponding to that for Recipe C with 3% by weight coloring pigment.

It can be seen from the data that the metal powder does not impair mechanical properties to any great degree. The use of metal powder can therefore be seen as highly advantageous, both optically and with respect to metal properties.

All of the recipes may be used with commercially available metal powders such as those used in the ink, paint, and coating industry or electroplating.

All coloring effects and mechanical properties will be found correspondingly for the same recipes, but without any silver content. The visually observed degree of coverage provides secure protection against plastic discoloration due to skin contact, and particularly perspiration.

The invention claimed is:
1. An orthopedic cushion, comprising:
a plastic material;
silver contained in the plastic material and functioning as an antibacterial agent, the silver remaining in the plastic material upon contact of the orthopedic cushion with skin of a wearer during use;
metal particles dispersed in the plastic material to conceal discoloration resulting from contact of the orthopedic cushion with the skin of a wearer during use, the metal particles including at least one of aluminum, aluminum alloy, bronze, titanium, and platinum;

wherein the orthopedic cushion is in the form of at least one of an amputation stump liner, a cushioning pad, a prosthesis covering, an orthotic cushion, a prosthesis shaft, a shoe sole insert, and an orthopedic stocking;

wherein a content of the metal particles is in the range of at least 0.01% by weight to 3% by weight.

2. The orthopedic cushion as claimed in claim 1, wherein the metal particles, as a supplement to the silver, is present in the form of powder particles, fine chips, or filaments.

3. The orthopedic cushion as claimed in claim 1, wherein the content of the metal particles at least 0.1% by weight.

4. The orthopedic cushion as claimed in claim 1, wherein the plastic material comprises a polymeric or copolymeric elastic plastic, soft plastic, or polymer gel.

5. An orthopedic article, equipped with an orthopedic cushion as claimed in claim 1.

6. The orthopedic cushion as claimed in claim 1, wherein the orthopedic cushion is coated on at least one side with a textile cover or is coated on one or both sides.

7. The orthopedic cushion as claimed in claim 1, wherein the orthopedic cushion is coated on at least one side with a thin deposited layer.

8. The orthopedic cushion as claimed in claim 7, wherein the thin deposited layer is a chemical vapor deposition (CVD) layer.

9. The orthopedic cushion as claimed in claim 1, wherein the plastic material contains pigments or dyes.

10. The orthopedic cushion as claimed in claim 1, wherein the metal particles are present in the form of powder particles, fine chips, flakes, scales, granules, or filaments.

11. The orthopedic cushion as claimed in claim 10, wherein the metal particles have a particle size between 1 μm and 100 μm, and a minimum particle thickness for the flakes of 0.1 μm.

12. A method of concealing discoloration in polymer materials in an orthopedic cushion, comprising:

providing a material composition comprising at least one polymer material, silver and metal particles, the silver being contained in the polymer material and functioning as an antibacterial agent, the metal particles being dispersed in the polymer material, a content of the metal particles being in the range of at least 0.01% by weight to 3% by weight of the material composition;

forming the orthopedic cushion comprising the material composition, the metal particles of the material composition concealing discoloration in the orthopedic cushion;

wherein the metal particles include at least one metal in the group consisting of aluminum, zinc, bronze, titanium, and platinum.

13. The method as claimed in claim 12 wherein the orthopedic cushion being selected from the group consisting of an amputation stump liner, a cushioning pad, a prosthesis covering, an orthotic cushion, a prosthesis shaft, a shoe sole insert, or an orthopedic stocking.

14. The method as claimed in claim 12, wherein the orthopedic cushion is coated on at least one side with a textile cover, or is coated on both sides with a textile cover.

15. The method as claimed in claim 12, wherein the metal particles comprise aluminum or an aluminum alloy.

16. The method as claimed in claim 12, wherein the metal particles are in the form of powder particles, fine chips, or filaments.

17. The method as claimed in claim 12, wherein the polymer material comprises a polymeric or copolymeric elastic plastic, soft plastic, or polymer gel.

18. An orthopedic cushion, comprising:
a plastic material;
silver contained in the plastic material and functioning as an antibacterial agent;
metal particles dispersed in the plastic material to conceal discoloration, the metal particles including at least one of aluminum, aluminum alloy, magnesium, bronze, titanium, and platinum;
wherein a content of the metal particles is in the range of at least 0.01% by weight to 3% by weight;
wherein the orthopedic cushion is in the form of an amputation stump liner.

19. The orthopedic cushion as claimed in claim 18, wherein the metal particles have a particle size between 1 μm and 100 μm.

The following is an examiner's statement of reasons for allowance: The prior art does not teach or suggest instant orthopedic cushion comprising a plastic material, silver and 0.01-3% metal particles.

* * * * *